(12) United States Patent
Raghavan et al.

(10) Patent No.: US 6,749,833 B2
(45) Date of Patent: Jun. 15, 2004

(54) DESIGN AND PLANNING SYSTEM FOR IMPROVING THE SURVIVAL RATE OF INJECTED STRUCTURES

(75) Inventors: Raghu Raghavan, Baltimore, MD (US); Timothy Poston, Singapore (SG)

(73) Assignee: BresaGen Limited, South Australia (AU)

( * ) Notice: Subject to any disclaimer, the term of this patent is extended or adjusted under 35 U.S.C. 154(b) by 0 days.

(21) Appl. No.: 09/866,524

(22) Filed: May 25, 2001

(65) Prior Publication Data

US 2002/0182583 A1 Dec. 5, 2002

(51) Int. Cl.[7] .............................................. A61K 49/00
(52) U.S. Cl. ...................... 424/9.1; 424/93.1; 424/93.2; 424/93.21; 604/181; 604/232; 604/191; 604/187; 604/199; 604/236
(58) Field of Search .............................. 424/93.21, 93.1, 424/93.2, 9.1; 604/181, 232, 191, 187, 199, 236

(56) References Cited

U.S. PATENT DOCUMENTS

| | | | | |
|---|---|---|---|---|
| 4,471,765 A | * | 9/1984 | Strauss et al. ................ | 128/1.1 |
| 5,980,885 A | | 11/1999 | Weiss et al. ............. | 424/93.21 |
| 5,993,462 A | | 11/1999 | Pomeranz et al. .......... | 606/129 |
| 5,997,525 A | | 12/1999 | March et al. ................ | 604/508 |

* cited by examiner

*Primary Examiner*—James Ketter
(74) *Attorney, Agent, or Firm*—Mark A. Litman & Assoc. P.A.

(57) ABSTRACT

The present invention includes a method for evaluating the acceptability of a device for the delivery of cells in a cell implantation therapy comprising:
  determining a first rate of cell survival in a stable environment,
  evaluating a second rate of survival during a procedure using a device that manipulates cells, and
comparing the first and second rates of survival to determine the effect of the device used during the procedure on cell survival rates to establish a base line effect of the manipulative procedure on cell survivability. That method may be practiced wherein after determining the second survival rate, modifying the design of the device, evaluating a third rate of survival after modifying the design of the device to determine if the change has increased the rate of survival during the procedure. The method is particularly effective where the procedure is selected from the group consisting of cell harvesting, cell transport, cell implantation, and cell delivery. The procedure may include, for example, a peristalsis process for movement of cells during the procedure or a bolus flow of cells for movement of cells during the procedure.

7 Claims, 12 Drawing Sheets

DESIGN AND PLANNING SYSTEM FOR IMPROVING THE SURVIVAL RATE OF INJECTED STRUCTURES

BACKGROUND OF THE INVENTION

1. Field of the Invention

Medical technology has advanced dramatically and swiftly over the past decades. The advances have been particularly significant within the fields of genetic engineering, cell technology, and in their proposed uses in actual therapies. For example, it is an increasingly common proposed medical technique to inject live cells into the human body. The intention of these cell implantation therapies (with genetically engineered cells or harvested cells) is to have the implanted cells attach to or settle into the tissues and provide their essential functions in their new location. The function of these therapeutic techniques may be to repair a genetic defect (producing a needed substance that the body is failing to create), repair traumatic damage, replace disease-diminished cells, contribute to the mechanical properties of an organ by the structures they build, and so forth. The science of cell implantation therapy is far in advance of the engineering technology needed to implement these therapies.

One engineering problem that is considered here is an appreciation of the fact that not all cells survive the injection process. When a substantial fraction of the cells fails to settle and function in the body, the efficacy of the treatment is much reduced. Although some cell deterioration is expected, there has been almost no consideration in the literature of this problem. There has been little publication on the design and engineering of delivery systems to reduce the impact of the delivery system on aggravating normal loss of viable cells.

Cells to be used for implantation are often grown on a substrate, rather than floating freely in nutrient. If this process fails, there are no cells to harvest, and treatment cannot be attempted on a patient. Where treatment fails to establish cells in the body, their survival may have been hampered in one or more of the stages of harvest (detaching them from the substrate and creating an injectable suspension), storage, transport within the system, injection, and motion through tissue before reattaching themselves. (If attached cells fail to survive or function as intended, the problems are most likely specific to the bioengineering of the particular cell line, and we do not address that problem here.)

U.S. Pat. No. 5,997,525 describes a system for delivering therapeutic or diagnostic agents to the heart, including a catheter that delivers the material to be delivered in a viscous carrier. The material may be delivered in association with an elongated, flexible transmission means for lasing that forms channels in the heart wall, as delivery locations.

U.S. Pat. No. 5,993,462 describes a shapeable catheter, which may include a pre-shaped region bent into a predetermined shape. A lumen may be proportioned to slidably receive a core wire. A pull wire may be provided to allow the user to cause deflection at a distal portion of the catheter.

U.S. Pat. No. 5,980,885 describes a method for inducing in vivo proliferation of precursor cells located in mammalian neural tissue. Simple glass pipettes are used to deliver the cell suspensions at levels of about 50,000 cell/microliter.

As can be seen from this review of the prior art, the delivery systems described tend to be essentially primitive tubes, with no consideration of flow functions or physical effects on cells during the delivery process. To assure that cell implantation becomes a viable procedure, it is essential that engineering considerations be used in the design of the pick-up, transportation and cell delivery devices.

SUMMARY OF THE INVENTION

Pick-up, transport and delivery systems for cell therapy and implantation procedures are designed and conceptual planning parameters are provided intended to increase the survival rate of cells used during these procedures. The systems provide various movement effecting systems that minimize stress on cells, which stress might damage cells, reduce their survivability, and/or reduce their ability to attach upon delivery. Such systems include, peristalsis flow, bolus flow, gradated (sloped) size exit ports, and other systems that reduce vortices, compressive effects, cell blocking effects, and other stresses.

BRIEF DESCRIPTION OF THE FIGURES

FIGS. 8a and 8b shows computed flow through a catheter tip, with intensity maps for shear in 8b and extension in 8a.

DETAILED DESCRIPTION OF THE INVENTION

Figure 1A:
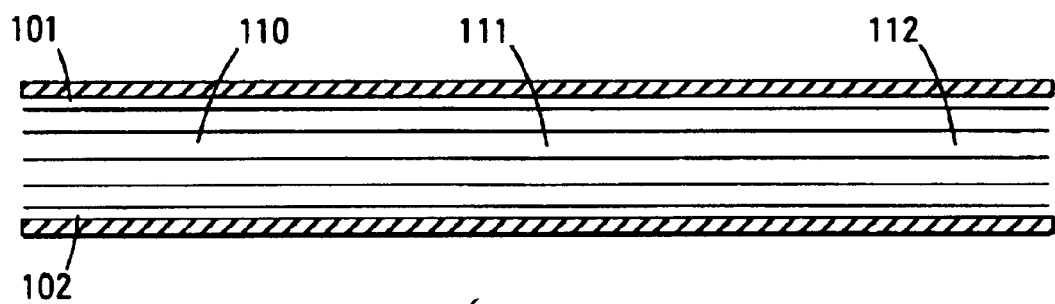
FIGS. 1a and 1b graphically describe a flow dominated by shear.
Figure 1B:
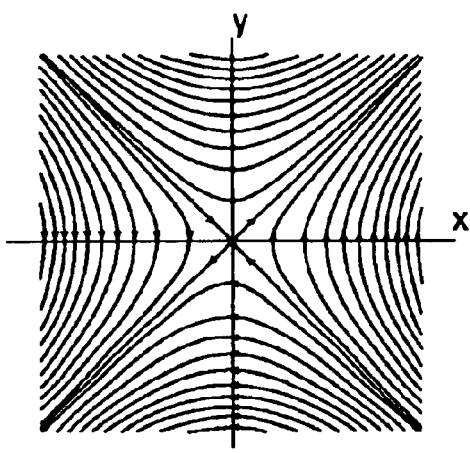
Figure 2:
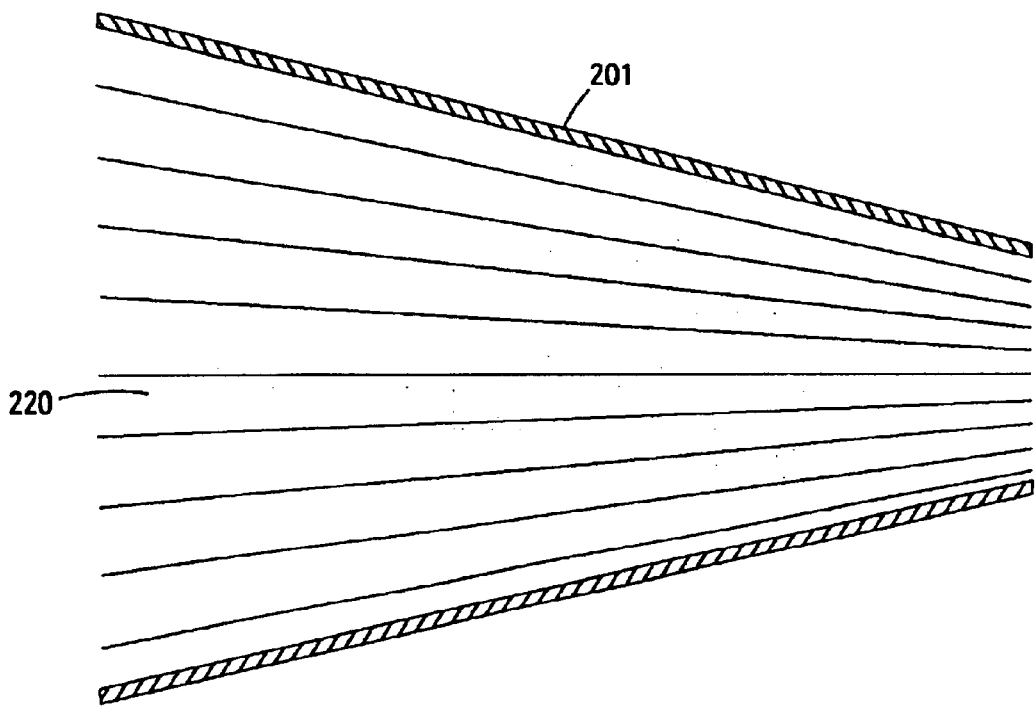
FIG. 2 describes a flow in which extension is important.

This invention attempts to address primarily the pick-up, transport and injection stages of the cell therapy implantation process. It is known and apparent from practical experience that injection through a nozzle can reduce the viability of cells, as by stress applied by the nozzle on the cells. Only in the case of a very fine hypodermic injection system does the internal nozzle diameter approach that of a cell to within a single-digit factor, so that in many cases of transport systems for cells (particularly in that of a catheter), one may assume that most cells do not encounter the nozzle wall. The inventors therefore assert that it is probable that any damage to cells occurring during delivery must be affected by features of the flow itself. Velocities are small enough that acceleration forces on the cell should be minimal or at least minor, and vorticity (a measure of the rotation of small elements of the fluid) is not high or non-uniform enough for the rotation of the cell to damage itself by centrifugal forces, or by twisting of the cell due to differential rotation of its parts. Damage is therefore asserted by the inventors to be typically due to the aspects of flow that act to deform its shape. A cell is highly adaptive in form, but it is not the flexible bag of viscous fluid as it is sometimes perceived to be. Changing shape can involve dissolving and rebuilding the cell cytoskeleton (in particular, the network of stiff microtubules) that supports that shape, as well as change in shape of the external membrane, for which membrane material must migrate to the enlarged regions. (In many ways the membrane resembles a 'surface fluid', in which external cell features like drug receptors circulate freely. But its flow rate is not arbitrarily high.) Forced deformation that occurs at a rate that is faster than this rebuilding process may cause rupture of internal processes or of the membrane, damaging the cell.

As fluid moves, even in a steady flow, any small region of the fluid moving with it commonly changes shape. (There are a few simple flows where this is untrue, but they do not include the injection process.) If the small region is replaced by a structure such as a cell, either the cell deforms as the fluid would, or the stiffness by which it resists deformation creates stresses that can damage the structure. To some extent, if the fluid is more flexible (less viscous) than the cells that they are carrying, the liquid will sacrificially deform in comparison to the cells and less stress will be placed on the cells, there will be less cell damage, and there will be a higher cell survival rate. However, altering the flow of even an inviscid fluid involves forces on the fluid, unless it is also massless. The reaction to this action on the fluid is still a stress on the cell.

The features of a flow that change the shape of a small region of fluid are shear and extensionality, as illustrated in drawings 1 and 2. We define these below as the quantities S and P, after first showing examples. Drawing 1a shows a steady incompressible two-dimensional flow in which shear dominates, with fluid 101 at the top moving faster than fluid 102 at the bottom of the figure. A square region 110 changes through forms 111 and 112, becoming an ever more slanted parallelogram. Similar deformations occur in three dimensions.

Drawing 2 shows a steady incompressible two-dimensional flow in which extension is more important than shear. (For simplicity, the example is one where the channel sides exert no frictional drag on the fluid.) As fluid passes through the narrowing channel 201 it moves faster, so that the total flow (which increases with either speed or cross-section) can remain the same, and fluid neither accumulates nor originates in the channel. A square region 220 becomes narrower, but maintains its area (in three dimensions, its volume), and thus becomes longer, evolving through narrower forms.

The present invention includes a method for evaluating the acceptability of a device for the delivery of cells in a cell implantation therapy comprising:

determining a first rate of cell survival in a stable environment, evaluating a second rate of survival during a procedure using a device that manipulates cells, and comparing the first and second rates of survival to determine the effect of the device used during said procedure on cell survival rates to establish a base line effect of the manipulative procedure on cell survivability. That method may be practiced wherein after determining the second survival rate, modifying the design of the device, evaluating a third rate of survival after modifying the design of the device to determine if the change has increased the rate of survival during the procedure. The method is particularly effective where the procedure is selected from the group consisting of cell harvesting, cell transport, cell implantation, and cell delivery. The procedure may include a peristalsis process for movement of cells during the procedure or a bolus flow of cells for movement of cells during the procedure. A resulting device for the movement of cells might comprise a source of cells, a source of a liquid carrier, and a combination zone within a liquid region for the liquid carrier, the combination zone inserting cells into said liquid carrier to form a bolus of cells within the liquid carrier. For example, the device may operate where the cells are provided from said source of cells within a medium that allows a bolus to be maintained during transport of the cells. For example, the bolus protects cells and improves their survival rate at a flow rate between 500 and 1000 cells per minute through the device as compared to cells flowing through said device without a bolus being present at the same flow rate. This method my be practiced wherein the procedure comprises the delivery of cells for cell implantation comprising transporting cells for delivery by a process that includes determining safety limits by at least one comparison with cell damage resulting from transporting effect wherein flow of cells is generated by enclosing a fluid carrying cells between two concentric parallel cylinders, which may be caused to rotate at different speeds. The process may be practiced wherein the flow is generated instead by enclosing the fluid in a tank containing six parallel rollers symmetrically placed in or near to a regular hexagonal arrangement, with approximately equal radii, of which three rotate clockwise and the rest, placed between them, rotate anticlockwise, at approximately equal rates. The safety limits are determined by subjecting the cells to flows of both types, so that the damage limits for shear and extensional flow may be separately determined.

A flow $V(x,y,z)$ gives a movement vector $(V^x(x,y,z), V^y(x,y,z), V^z(x,y,z))$ at each point $(x,y,z)$. (We ignore here variation with time.) Its effect on a small region U around $p=(x_o,y_o,z_o)$ is approximated by the effect of its local linearization, the flow corresponding to the flow:

$$\overline{V}\begin{bmatrix} x_0 + X \\ y_0 + Y \\ z_0 + Z \end{bmatrix} = V(x_0, y_0, z_0) + \begin{bmatrix} \frac{\partial v^x}{\partial x}(p) & \frac{\partial v^x}{\partial y}(p) & \frac{\partial v^x}{\partial z}(p) \\ \frac{\partial v^y}{\partial x}(p) & \frac{\partial v^y}{\partial y}(p) & \frac{\partial v^y}{\partial z}(p) \\ \frac{\partial v^z}{\partial x}(p) & \frac{\partial v^z}{\partial y}(p) & \frac{\partial v^z}{\partial z}(p) \end{bmatrix} \begin{bmatrix} X \\ Y \\ Z \end{bmatrix} \quad (1)$$

$$= V(p) + \underline{V}_p \begin{bmatrix} X \\ Y \\ Z \end{bmatrix} \text{ for short.} \quad (2)$$

The 0-order term $V(p)$ moves U from point to point; change in shape is dominated by the structure of $\underline{V}$ as the sum of its symmetric part $$\underline{V}^S = \tfrac{1}{2}(\underline{V}-\underline{V}^T) \quad (3)$$

And its skew-symmetric part $$\underline{V}^R = \tfrac{1}{2}(\underline{V}-\underline{V}^T) \quad (4)$$

If $\underline{V}=\underline{V}^R$, the change in U due to $\underline{V}$ is purely rotational, so we may consider $\underline{V}^S$ as the part describing 'strain', or change in shape. It is appropriate to compute the size of this part as one measure of shear strain in the fluid and by implication, shear stress on cells or other structures moving with the fluid. However, particularly for structures that are not close to spherical, this stress can be somewhat transient, even in a uniform flow. The two-dimensional vector field $$V(x,y)=(2y,0) \quad (5)$$

Gives a flow such as is shown in Drawing 1. Being linear, it coincides with its linear approximation: we have $$\overline{V}\begin{pmatrix} x_0 + X \\ y_0 + Y \end{pmatrix} = V(x_0) + \begin{pmatrix} 0 & 2 \\ 0 & 0 \end{pmatrix}\begin{pmatrix} X \\ Y \end{pmatrix}, \quad (6)$$

$$\underline{V} = \begin{pmatrix} 0 & 2 \\ 0 & 0 \end{pmatrix} \quad (7)$$

for any point $p=(x_0,y_0)$. For this we have $$\underline{V}^R = \begin{pmatrix} 0 & 1 \\ -1 & 0 \end{pmatrix}, \quad (8)$$

corresponding to clockwise rotation with angular velocity 1, and $$\underline{V}^S = \begin{pmatrix} 0 & 1 \\ 1 & 0 \end{pmatrix}, \quad (9)$$

a saddle flow with $$\underline{V}^S \begin{pmatrix} 1 \\ 1 \end{pmatrix} = \begin{pmatrix} 1 \\ 1 \end{pmatrix} \quad (10)$$

$$\underline{V}^S \begin{pmatrix} 1 \\ -1 \end{pmatrix} = -\begin{pmatrix} -1 \\ -1 \end{pmatrix}, \quad (11)$$

as shown in Drawing NN. Under this flow a rectangular region with sides parallel to the diagonal lines x=y and x=−y will move along the curves shown, remaining rectangular and keeping becoming longer in the x=y direction, shorter in the x=−y direction. These principal directions do contain information about the stress on an object moving with the flow V, but (due to the rotation element $\underline{V}^R$) in a directionally transient way. In a round object, the directions change within the object: a long one turns until it is close to parallel with the x-axis. In that direction, lengths are not increasing (as is visible with the base of the region tracked in Drawing 1a), so the forces tending to stretch the object in its lengthwise direction diminish. The x-direction is a principal direction (eigendirection) of $\underline{V}$, belonging to the eigenvalue 0: a vector pointing in that direction continues to do so, with growth rate 0.

This is in contrast to the evolution of a small region in a flow like Drawing 2, where a small region that is long in the x-direction continues to grow in that direction, so that for an object in the flow that is unable to grow, stress is unceasing. In general a small region $\underline{U}$ will grow, and a narrow rigid object will turn, in the direction of the largest eigenvalue of the linearized flow, so that stretching stress in that direction continues to apply over the object's length. The sustained effect of such an extensional flow on some objects moving with the fluid, such as polymer molecules, is known to be substantially greater than for 'pure shear' flow like (5): we have found no studies of its effects on cells, but the present invention includes assessment of such effects, as well as those of shear.

Motivated by these considerations, we define two scalar measures of deformational tendency for a flow of V at a point p, both invariant under rotation of the coordinate system used in its description. The first is the shear level S, being the size of the corresponding $\underline{V}^S(p)$ as measured by the square root of the sum of the squares of its matrix entries. The second is the persistent strain level P, given by root mean square of the eigenvalues of $\underline{V}_p$. (An alternative measure is to use the largest of the eigenvalues. However, to do so would be more computationally expensive.) For (5), with the repeated eigenvalue 0, we have P=0.

To compute P, it is not necessary to find the eigenvalues explicitly. For any 3×3 matrix $$A = \begin{pmatrix} a_1^1 & a_2^1 & a_3^1 \\ a_1^2 & a_2^2 & a_3^2 \\ a_1^3 & a_2^3 & a_3^3 \end{pmatrix} \quad (12)$$

with eigenvalues $\lambda_1$, $\lambda_2$ and $\lambda_3$ we have $$\lambda_1\lambda_2\lambda_3 = \det A = a_1^1 a_2^2 a_3^3 - a_1^1 a_3^2 a_2^3 - a_1^2 a_2^1 a_3^3 - a_1^2 a_3^1 a_2^3 - a_1^3 a_2^1 a_3^2 - a_1^3 a_3^1 a_2^2 \quad (13)$$

$$\lambda_1\lambda_2 + \lambda_1\lambda_3 + \lambda_2\lambda_3 = \det a^2 a^2 + \det\begin{pmatrix} a_1^1 & a_2^1 \\ a_1^3 & a_2^3 \end{pmatrix} + \det\begin{pmatrix} a_1^1 & a_3^1 \\ a_1^3 & a_3^3 \end{pmatrix} + \det\begin{pmatrix} a_2^2 & a_3^2 \\ a_2^3 & a_3^3 \end{pmatrix} \quad (14)$$

$$= a_1^1 a_2^2 - a_2^1 a_1^2 + a_1^1 a_3^3 - a_3^1 a_1^3 + a_2^2 a_3^3 - a_3^2 a_2^3 \quad (15)$$

$$= K(A) \text{ for short,} \quad (16)$$

$$\lambda_1 + \lambda_2 + \lambda_3 = \text{trace } A = a_1^1 + a_2^2 + a_3^3 \quad (17)$$

This gives $$(\lambda_1+\lambda_2+\lambda_3)^2 = (\lambda_1^1+\lambda_2^2+\lambda_3^3) + 2(\lambda_1\lambda_2+\lambda_1\lambda_3+\lambda_2\lambda_3) \quad (18)$$

so that for $A=\underline{V}_p$ we have $$P = \sqrt{(\text{trace } \underline{V}_p)^2 - 2K(\underline{V}_p)}. \quad (19)$$

In the case of the flow of an incompressible fluid, where the trace must identically vanish, this reduces to $$P = (-2K(\underline{V}_p)). \quad (20)$$

Analogously to the injection of cells, other large structures in suspension may be injected into tissue, such as macromolecules and nanotechnology devices. Many of these remain to be invented, but in many cases will be similarly sensitive to deformational forces that can disrupt their internal structure.

We are able to test cells or other structures in suspension for vulnerability to shear stress by placing them in suspension in a Poiseuille flow dominated by shear, such as between two cylindrical walls, and for vulnerability to extensional stress in a flow driven by six rollers, as in the polymer experiments described by Berry and Mackley. ("Six-roll mill—unfolding an unstable persistently extensional flow", Proc. Roy. Soc. A 287 (1337) 1–8, 1977.) We assess the viability of the injected entities, for instance by fluorescence if the gene for green fluorescence protein has been coupled to a critical step in the life process of injected cells, which is now routine genetic engineering. This enables us to limit the viability reduction from the exposure of cells to these deformational stresses.

In planning an injection or designing an injection device, we solve for the flow in the catheter or syringe, through the nozzle, and emerging into the tissue, using data for the injection pressure or flow rate, the geometry of the device, the anatomy of the target region, and the background pressure in the tissues. We then compute the levels of shear and extensional strain, and the exposure times. If these are predicted to reduce viability below acceptable levels, we reduce injection rate or pressure, or modify the catheter geometry, before performing the injection. This affects both the design of a delivery system to be delivered by manufacturers, and a clinician's choice of elements within that system and of settings for a particular injection We describe a system first for the design of an injection process for structures in suspension, and then for the use of it. In determining a quantifiable basis for the measurement of the efficacy of the practices of the present invention, a population of cells may be tested for viability in various ways. For instance, one may withdraw a sample, and test how well these cells attach themselves to a laboratory substrate and multiply there. Alternatively, one may stain a sample (usually fatally) to measure some characteristic of the cells associated with health. Alternatively, one may examine the cells in a transparent suspension through a microscope, to discover abnormalities in transparency, color, shape, or fraction of cells in the process of cell division. In our preferred embodiment, however, the cells used for testing the performance of the devices on cell survival are genetically modified to express a gene for green fluorescence protein (GFP) simultaneously with some biochemical process such as glucose metabolism or protein synthesis characteristic of good health for that cell type. The test then consists simply of shining ultraviolet light on the cells, and measuring the brightness of the emitted light per cell. When we write 'test for integrity' below, therefore, we preferentially mean this test, but the use of any other test that exists now or in the future falls within the logic of the present invention. If the structures in suspension are macromolecules, a range of chemical tests will provide data on their integrity. Similarly, the development process for nanodevices will provide ways to test their integrity, each according to their kind.

Figure 3:
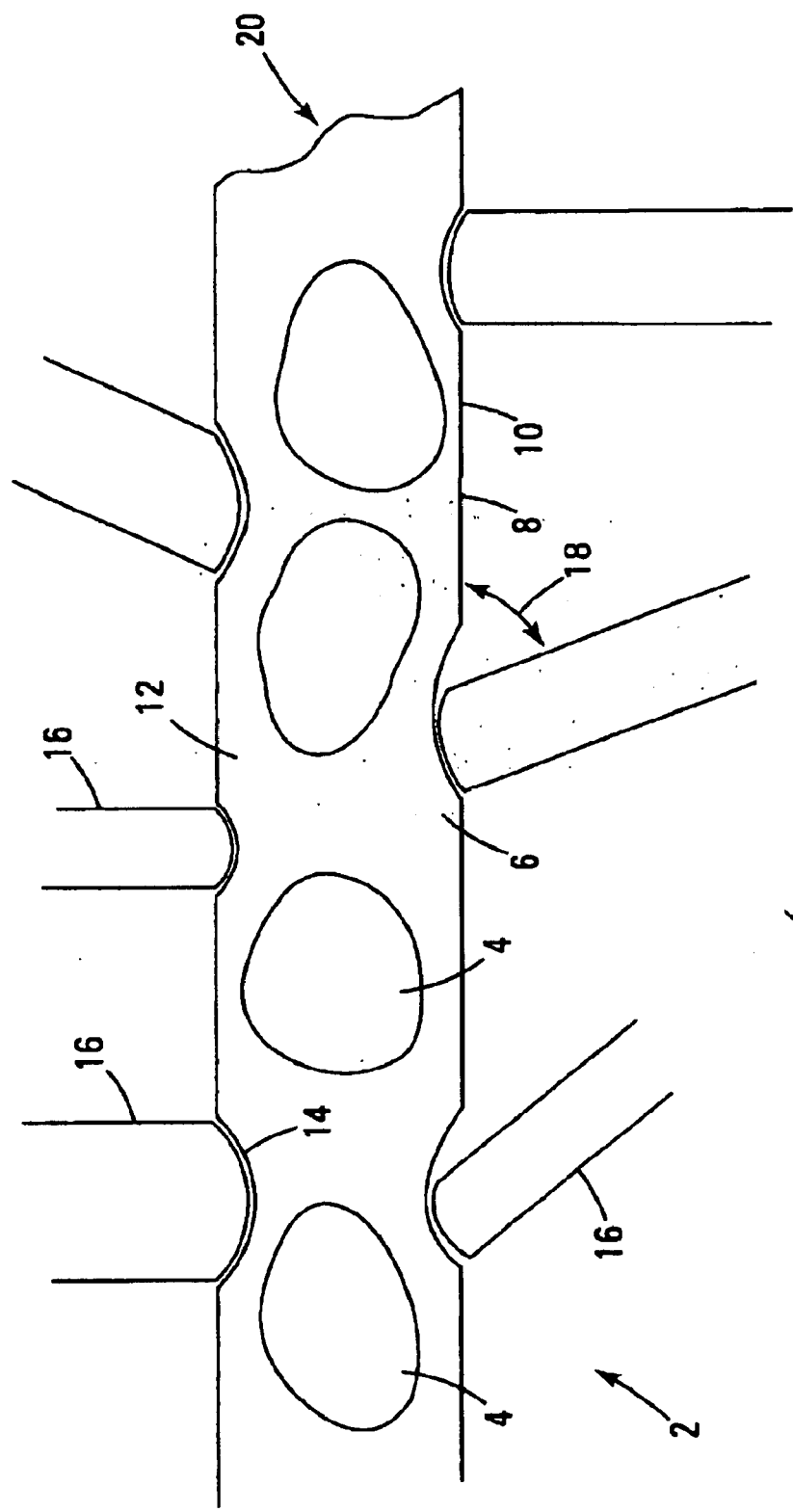
FIG. 3 shows a section of a delivery catheter with peristalsis flow to deliver cells.

FIG. 3 shows a tube carrying system 2 where the flow of cells 4 in a liquid carrier 6 through a tubular element 8 is motivated or moved by a peristalsis mechanism. The surface 10 of the tube is shown to have regions of larger diameters 12 and smaller diameters 14. These variations in diameters can be effected by any of the various available systems that can be used to create a peristalsis effect on the tube. The mechanism shown in FIG. 3 is the most simplistic, comprising contracting elements 16 that, in series, respectively contract and relax, preferably at a slight angle 18, thereby creating a peristalsis effect as the contractions gently propel the cells 4 and liquid carrier 6 through the interior 20 of the tubular element 8. The important concept to appreciate is that the contractions in the area of the smaller diameters 14 is not intended to apply direct pressure to the cells, but rather to maintain the flow of liquid carrier 6 through the tubular element 8. By using the fluid flow pressure rather than physical pressure on the cells, there is less stress applied as only such pressure is necessary to continue the fluid motion of the liquid through the tube, rather than requiring sufficient pressure to overcome static inertia of a cellular mass.

Figure 4:
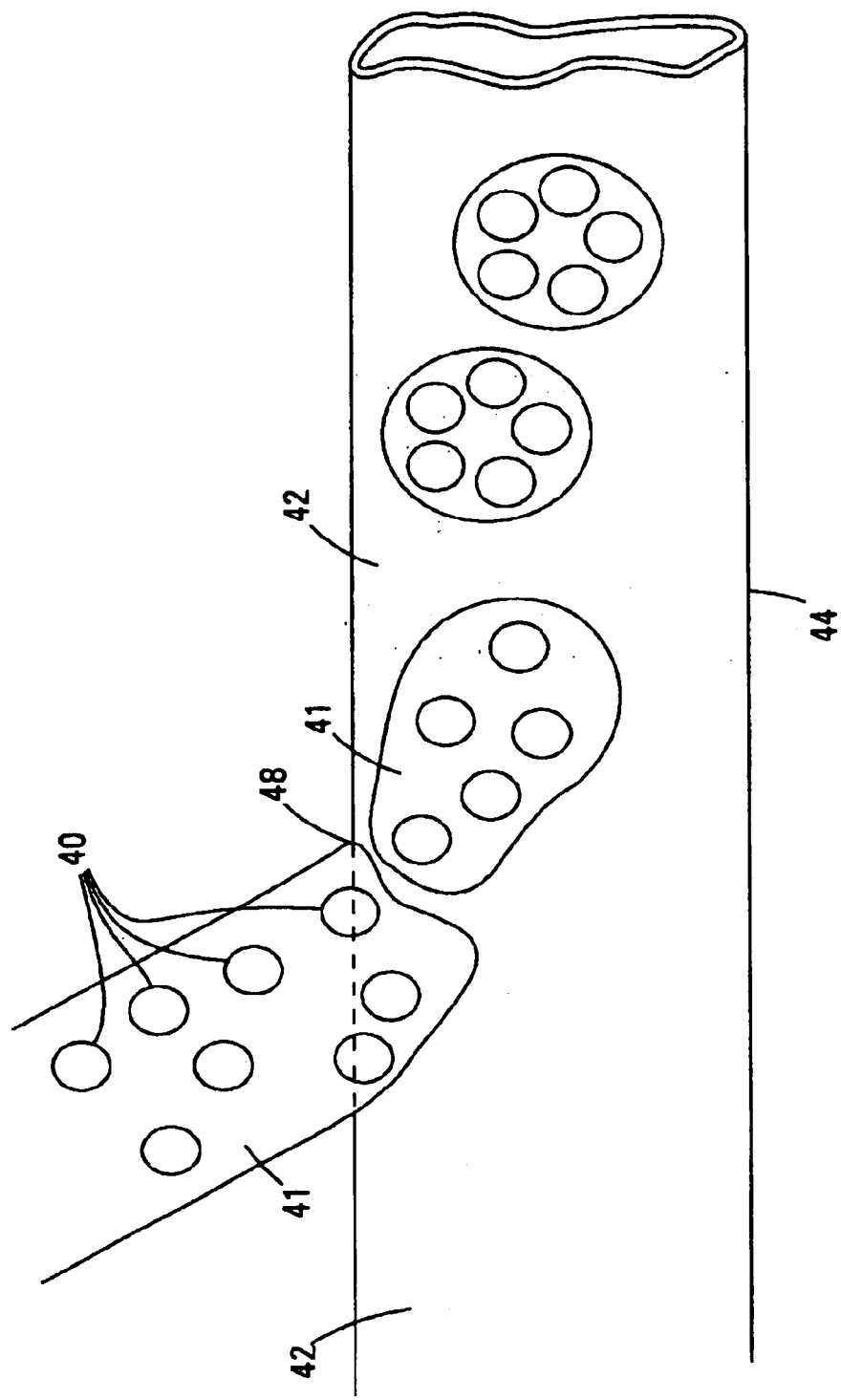
FIG. 4 shows a section of a delivery catheter with bolus flow to deliver cells.
Figure 5:
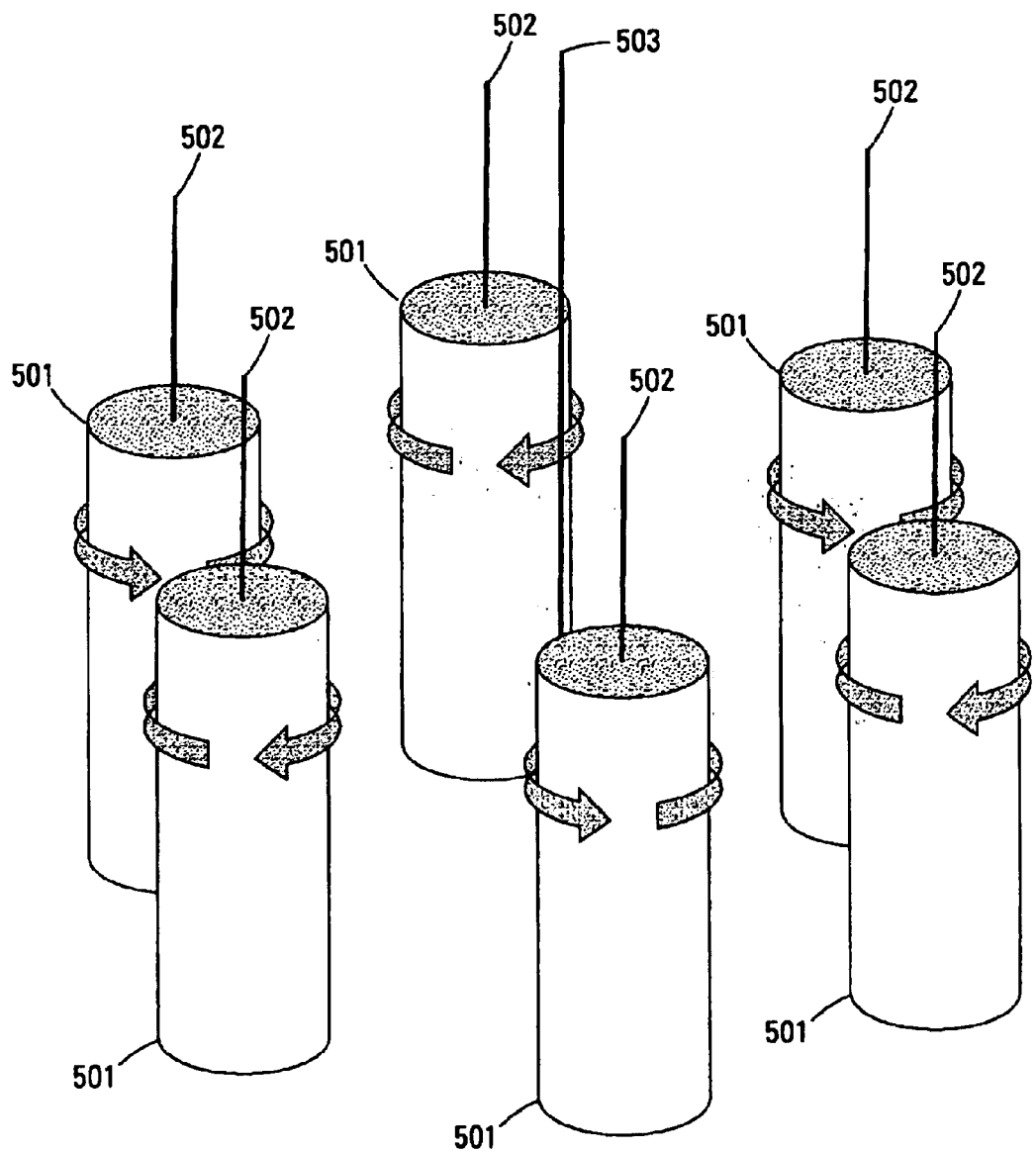
FIG. 5 shows an extensional flow apparatus.
Figure 6A:
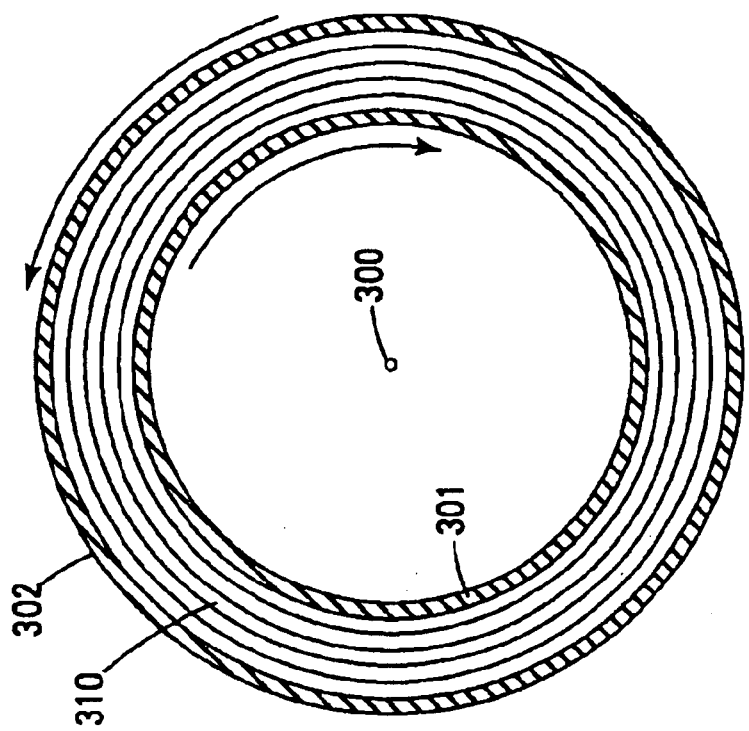
FIG. 6 describes a shear flow apparatus, driven by concentric rotating cylinders.
Figure 6:
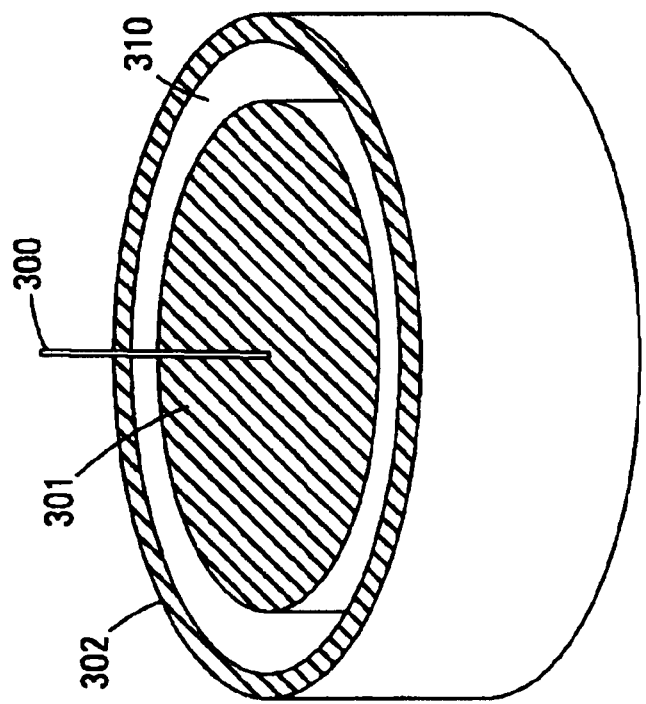
Figure 7A:
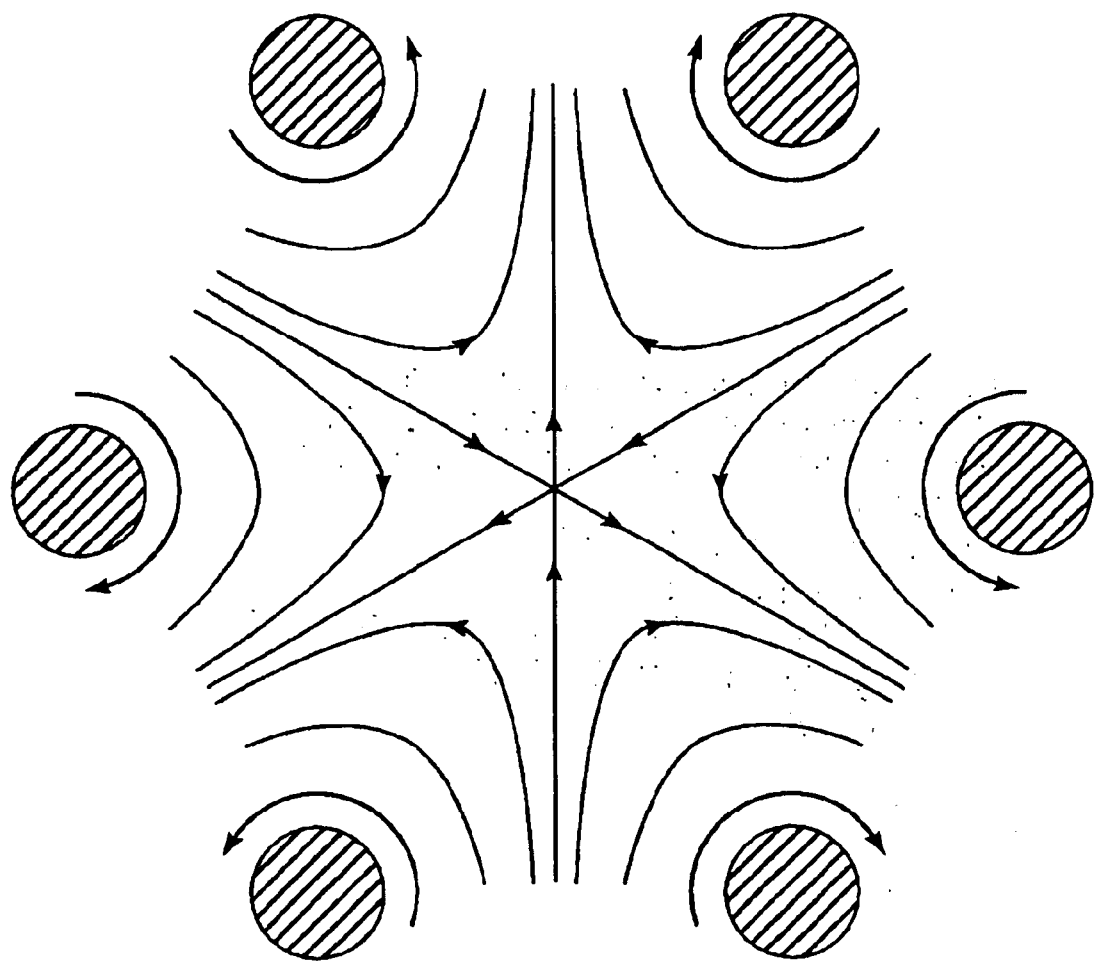
FIGS. 7a and 7b show flows dominated by extensionality, driven by counter-rotating rollers.
Figure 7B:
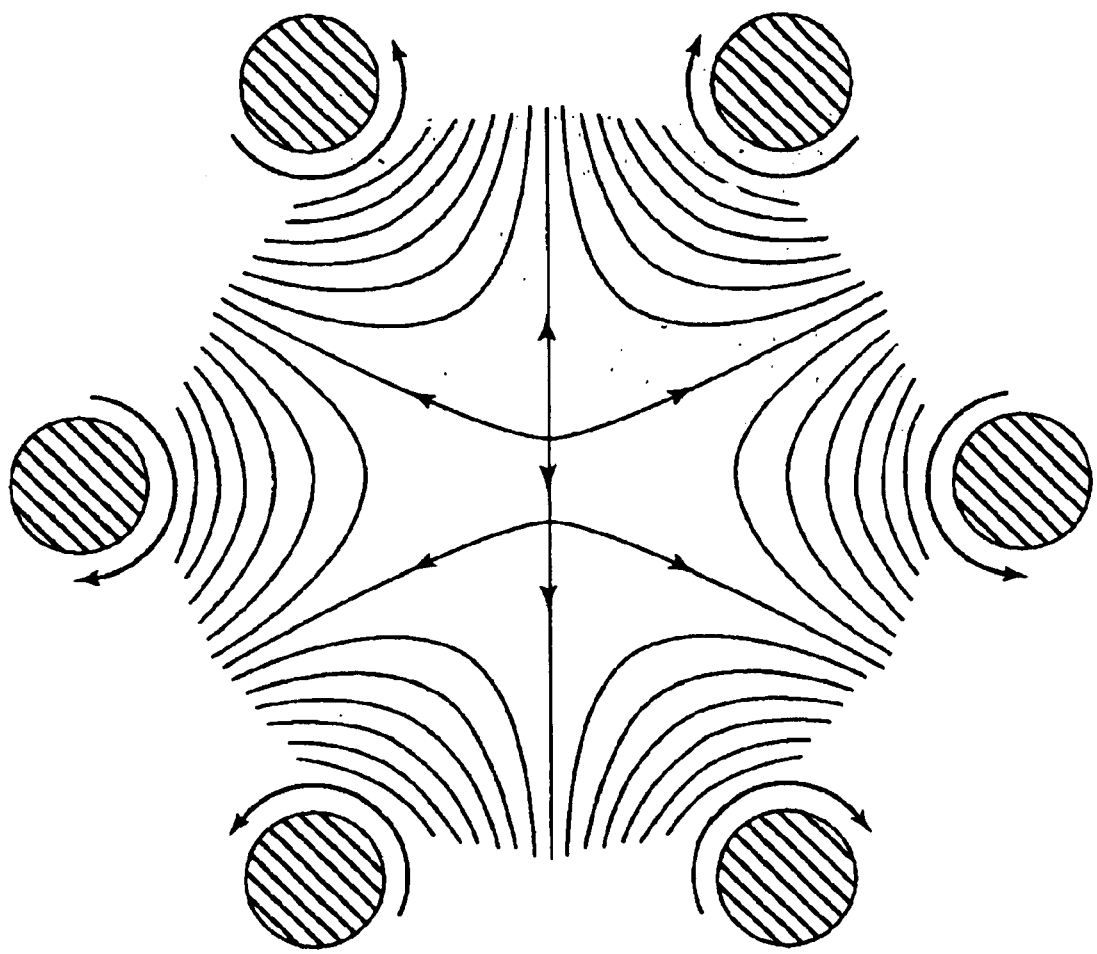
Figure 8A:
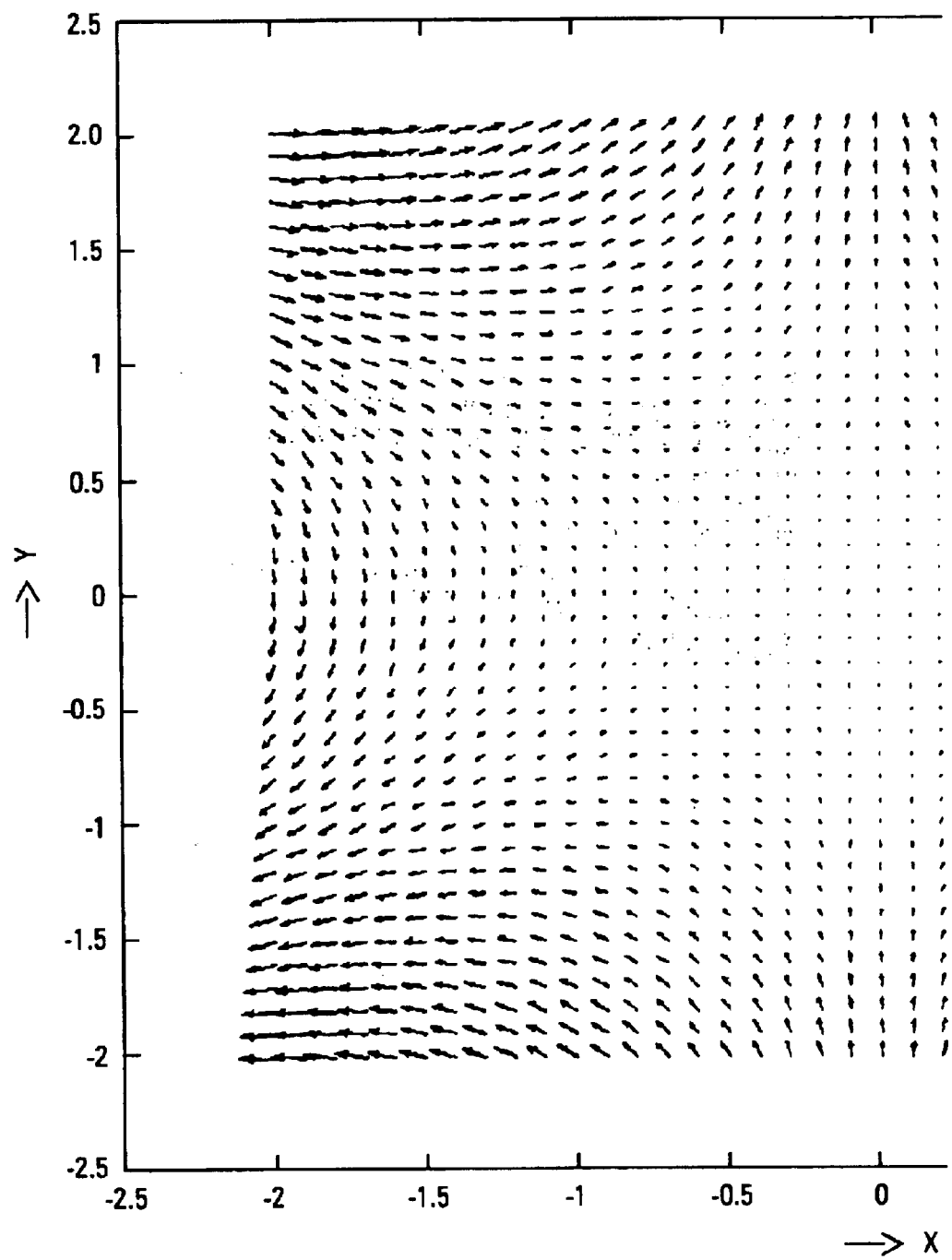
Figure 8B:
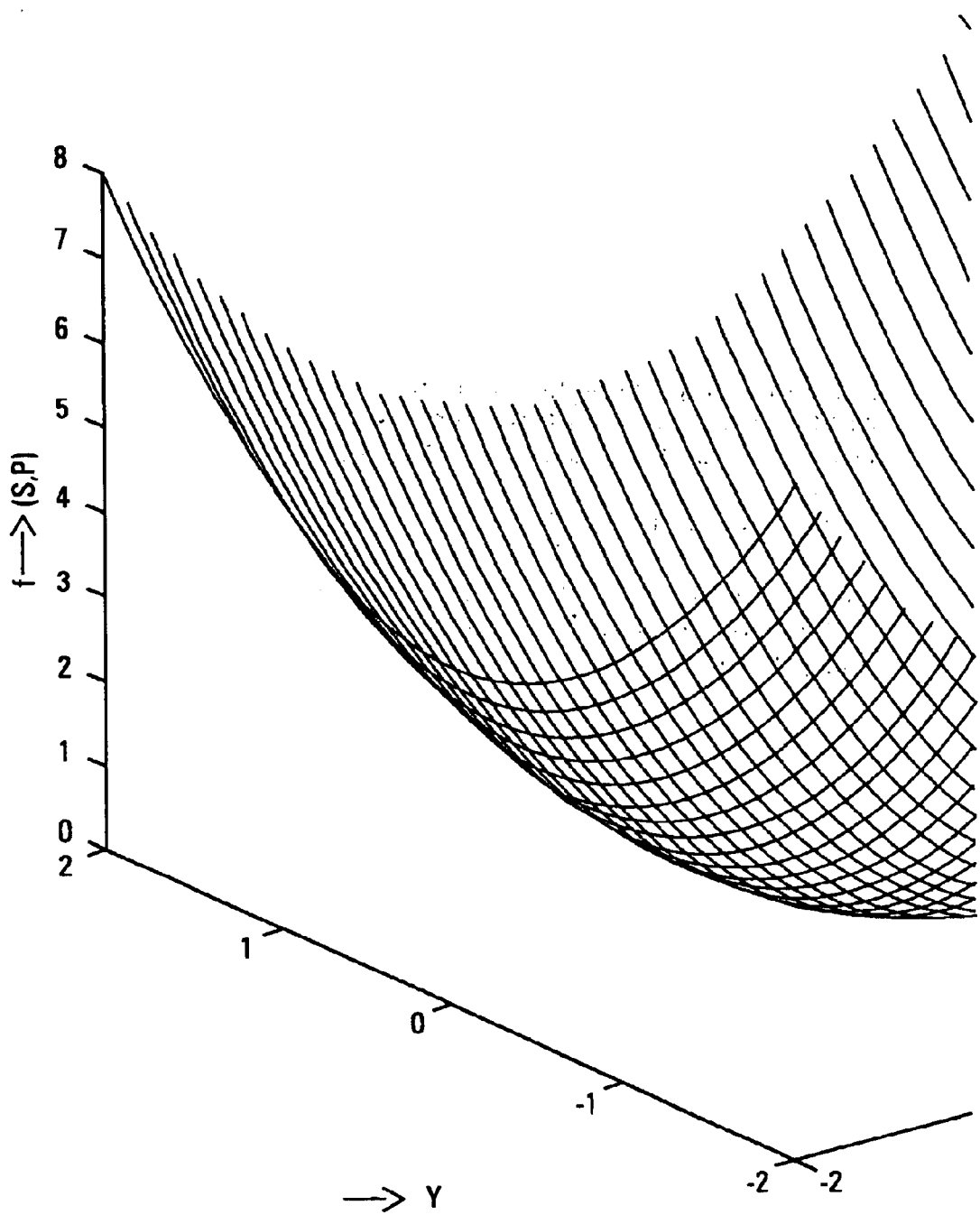

FIG. 4 shows a bolus flow of cellular masses 40 in a first fluid medium 41 carried in a second fluid medium 42 through a hollow tube 44. The cellular masses 40 are inserted into the fluid medium 42 at an injection site 44. Although this injection site 44 can cause some stress on cells, the fact that this stress would occur at only a single point in the transportation rather than continuously throughout the transportation process is an improvement. The structure and flow patterns at the injection site should also be evaluated to assure minimal cell damage at this point. The purpose of the bolus flow system is to reduce even the pressure effects upon cells by adding a cushioning or deflecting layer of a second fluid around the cells. The cells may be surrounded as a mass of cells (appropriately sized masses to facilitate attachment as a whole group) in a first fluid carrier in a second fluid phase that will not readily co-dissolve or dissolve in the first fluid carrier. The fluids may thus differ in hydrophobicity/hydrophilicity, ionic state (positive versus negative), or the like, as long as both fluids (which will be introduced into a patient) are tolerable by the organism into which they are being introduced. A digestible oil carrier would be suitable for the aqueous liquid that carries the cells, as would any other digestible or indigestible (inert) organic liquid. Fatty liquids would be useful, as would non-fatty liquids. The second fluid phase may thereby act as a food or nutrition source for cells, and could contain vitamins, minerals, enzymes, hormones, enhancers or the like to assist in the likelihood of a successful cell implantation.

A design procedure for a cell injection process for the present invention may then be defined as follows.

Harvesting of cells and the performance of storage tests on the cells to determine a basal stability state. To effect this process, first, harvest a sample of the cells from a substrate on which they are grown, and test them for health. If the cells fail at this stage, revise the harvesting process. (If it is a failure caused by mechanical stress, it is necessary to find a less damaging mechanic step; if the failure involves a chemical agent that causes the cells to release the substrate so that they can be harvested by a flow, it is necessary to find a better release agent.

If harvesting does not appear to damage the cells, the cells may be tested for health after a storage time typical of that expected in clinical use. If at the end of such a period the cells are less viable, improve the storage conditions (medium, temperature, time limit, etc.) until the health of at least F % of the cells appears unaffected by storage, where F is a percentage heuristically chosen. This measurement will also define a basal state for comparison with the transfer/application system against which the performance of the delivery system can be compared (as against a non-stressful storage condition).

In the case where the structures in suspension are macromolecules or nanodevices, the quality control procedures developed for their production will replace the harvesting test, and storage criteria will be part of their technical specification.

Design Features

It is important that components of the transport, pick-up or delivery system minimize elements or features that can stress or damage cells used in the cell implantation therapies contemplated in the practice of the invention. The following systems are discussed as potential elements in that system.

Needleless Connectors Between Segments of the Delivery System.

In one embodiment, at least one needleless connector between sections of the device may be a valve including a valve body configured as a Luer fitting. The valve also includes a resilient valve member disposed in the valve body and defining an outer periphery that is uninterrupted within the periphery. The valve member is biased to a first configuration, wherein a passageway for fluid communication is not established through the connector. In accordance with the present invention, the member is deformable to a second configuration, wherein fluid communication through the opening is permitted. As disclosed in detail below, the valve can include a male valve element disposed in the valve body. This valve element defines an engagement surface that extends outwardly beyond the valve body for contacting a spikeless/needleless connector to cause the valve element to move against the valve member and deform the valve member to the second configuration.

If desired, a protective collar can be connected to the valve body and extend away therefrom. In one embodiment, the collar is a tamper-evident collar having ratchet teeth. In another embodiment, the valve member is formed with a skirt defining a surface having an opening formed therein. Also, a flow constrictor can be engaged with an IV line for regulating cell-bearing fluid flow therethrough.

In another aspect, a valve between segments may include a valve body configured as a Luer fitting and a resilient valve member disposed in the valve body and biased to a first configuration, wherein a passageway for fluid communication is not established through the valve body. Per the present invention, the member is deformable to a second configuration, wherein fluid communication through the valve body is permitted. A male valve element is disposed in the valve body, and the valve element defines an engagement surface that extends outwardly beyond the valve body for contacting a spikeless/needleless connector to cause the valve element to move against the valve member and deform the valve member to the second configuration.

A Foley catheter adaptor may be used. Specifically, a male reflux valve that has a tapered body, with an elongated valve element reciprocally disposed for urging a valve member to an open configuration. The valve element does not have a Luer fitting contact flange. A valve can have a valve element formed with a Luer fitting contact flange. Also, a valve may have has a central guide extending into a valve element. Further, the lower needleless connector can be a female member valve or male member valve. Also, the lower needleless connector can be a reflux valve made by Clave, or a so-called "safe site" female reflux valve made by Burron or other female reflux valve. Further, the lower needleless connector can be a connector made by Baxter and referred to as an "interlink style connection". And, the lower needleless connector can be a female disc valve having a barbed shaft that is insertable into the tube, or a male disc valve having a bulkhead fitting configuration as shown. The bulkhead fitting can advantageously be similar to any one of the Luer bulkhead fittings made by Value Plastics, Inc. of Fort Collins, Colo.

The materials used in the construction of the delivery element may include polymers, ceramics, bioacceptable metals and alloys, composites, and the like, such as one of any of the currently available biocompatible materials, including but not limited to silk, nylon, plastic, polymer, ceramics, composites, metal, cells, collagen, bone or other material described above in connection with the definition of the term "filament". Specifically, the material may also be one of any available suture materials such as polyglycolic acid (PGA), polytetrafluoroethylene (PTFE), DACRON® polyester, polypropylene, nylon (polyamides), Perylene® polymer, polyester, silk, polybutylester, stainless steel, titanium, chromic gut, polybutylester, cotton, silver or the like. Here, cells may be injected into a created cavity within the body. Cells are passed down the shaft along with a controlled pressurized fluid from a storage chamber propelled by a pressure source. The fluid may then be withdrawn via a channel by a suction source. The pressure and suction sources may be manually activated or may be electronically controlled or otherwise controlled. The pressurized fluid may be also a gas like $CO_2$, but may also be an aqueous liquid such as saline solution, with other potential additives present in the carrier, such as dextrose, antibiotic or other biocompatible agent that acts either passively to assist the cells to reach their destination, or perform another purpose such as providing antibiotic protection, activating or sustaining the cells once in place, or providing a means through which the cells may be held in one place. The cells may be of any size that permits them to be introduced down the shaft of a cannula, catheter or needle.

Insofar as the driving forces are concerned, the word 'hydrostatic' will refer to fluid dynamics brought about by imposing a positive or negative pressure on a liquid within a microcatheter, as by the application of a microdialysis pump or vacuum, while 'hyperosmolar' will refer to fluid dynamics brought about by the use of a solute of sufficient size and concentration within a microcatheter to cause osmotic flow of fluid from surrounding tissue and into, or out of, the microcatheter. In contrast, the word 'diffusion' will refer to the spreading or intermixing of materials (fluids, dispersions, emulsions and/or solutes), due to molecular movement.

Those skilled in the relevant art, given the present description, will understand the manner in which any suitable combination of hydrostatic, hyperosmolar and diffusional forces can be employed to deliver and recover fluids and/or solutes using microcatheters in the manner provided herein. In general, the method and apparatus of this invention can be used in a site-specific manner to achieve any of a number of goals, including removing excess fluid (and thereby reduce interstitial pressure and improve microcirculation), and to deliver and/or recover agents to or from various parts of the body.

An example of an osmolar (e.g., hyperosmolar) microcatheter apparatus that may be used in conjunction with the more mass delivery component of the cell delivery system of the present invention includes a coaxial microcatheter in which a hyperosmolar perfusate is delivered by hydrostatic (i.e., pressure) means to the distal end of a coaxial microcatheter assembly, whereupon it returns to the pump reservoir together with tissue fluid that is recovered through the semipermeable outer membrane of the assembly by osmosis. Optionally, and preferably, the hyperosmolar perfusate itself contains a sufficiently high concentration of one or more agents to allow the agent to be delivered through the semipermeable membrane and into the tissue by diffusion or other forces. Examples of the use of hydrostatic and diffusion microcatheters include, respectively, the dual catheter and transdialysis embodiments.

In particular, one embodiment of the apparatus may be designed to perform 'transdialysis' using microcirculation, by the recovery and delivery of factors such as biological mediators and stimulating factors between different portions (e.g., healthy and injured) of the tissue and cells. Such an apparatus would have both a microcatheter component and a delivery pump reservoir. The delivery lumen and recovery lumen are separated by impermeable barriers and surrounded by semipermeable membrane. Optionally, the delivery and recovery lumen (in the form of conduits or passageways) can be provided in any suitable form, e.g. in the form of discrete microporous catheters, separated by a barrier to separate and prevent direct contact between the two.

Alternatively, a catheter could be employed to deliver cells incorporated in a biocompatible, biodegradable aqueous-soluble binder (e.g., sugar, carbohydrate, etc.) or polymer matrix. Suitable polymers may include polyvinyl alcohol, polyvinylpyrrolidone, low molecular weight water-dispersible polymers, amylopectin, collagen, mannitol, sorbitol, starch, sugars, saccharides, and the like. Unsuitable polymeric materials may comprise polyurethane, polydimethylsiloxane, ethylene vinyl acetate, polymethyl methacrylate, polyamide, polycarbonate, polyester, polyethylene, polypropylene, polystyrene, polyvinyl chloride, polytetrafluoroethylene and cellulose acetate or a mixture of the above or copolymers. These biodegradable polymers are optional and may be employed as hollow reservoirs or other structures. Additionally, pharmacologically inert fillers may be employed to tailor the time release degradability of the carrier for the cells. Various means for employing polymer compounds to secure a therapeutic agent are disclosed in Levy et al., WO 94/2123.

Flow Sensitivity Tests

If harvesting and storage pass the above tests, the structures should be submitted in suspension to a flow in which shear is dominant, as uniform as possible, and persistent. A representative flow of this type (Drawing 5) is that between an inner cylinder 301 and an outer cylinder 302 of radii $r_i < r_o$ respectively, rotating at different angular speeds of $s_i$ and $s_o$ per second respectively around a common axis 300, in which one of the speeds may be zero. (That is, either the inner or the outer cylinder may be fixed, but not both.) We take the positive sense of rotation as counterclockwise, viewed from above. The fluid 310 adjusts to move at speed $2\pi s_i r_i/\sec$ where it touches the inner cylinder 301, and at speed $2\pi s_o r_o/\sec$ where it touches the outer cylinder 302. For a suitable range of Reynolds numbers the flow moves any point of the fluid in a circle of radius r between $r_i$ and $r_o$ around the axis 300, at a speed well approximated by $$s = a + b \ln r \tag{21}$$

where $$b = \frac{(s_0 - s_1)}{(\ln r_0 / r_1)} \tag{22}$$

$$a = s_0 - b \ln r_0. \tag{23}$$

This gives a flow velocity, in coordinates where the upward axis 300 is the positive z-axis, of $$V(x, y, z) = (sy, -sx, 0) \tag{24}$$

$$= (a + b\ln r)y, -(a + b\ln r)x, 0) \tag{25}$$

$$\underline{V}_p = \begin{pmatrix} \frac{bxy}{r^2} & \frac{by^2 + r^2(a + b/\ln r)}{r^2} \\ \frac{-bx^2 + r^2(a + b/\ln r)}{r^2} & \frac{bxy}{r^2} \end{pmatrix} \tag{26}$$

$$\underline{V}^R = \begin{pmatrix} 0 & b + 2a + 2b\ln r \\ -(b + 2a + 2b\ln r) & 0 \end{pmatrix} \tag{27}$$

$$\underline{V}^S = \begin{pmatrix} \frac{2bxy}{r^2} & \frac{b(y^2 - x^2)}{r^2} \\ b(y^2 - x^2) & \frac{-2bxy}{r^2} \end{pmatrix} \tag{28}$$

$$S = b\sqrt{2} \tag{29}$$

$$P = \sqrt{((a + b + b\ln r)(a + b\ln r))} \tag{30}$$

For sample values $r_0=9$, $r_1=10$, $s_0=0$, $s_1=1$, this gives the shear level as a uniform S=13.42. The persistent strain level in the middle of the channel, with r=9.5, is only P=2. 267. By adjusting either or both speeds, this apparatus thus allows us to subject the structures in suspension to controlled and quantified shear stress, and test their health after timed exposure to various known levels of shear, with less extensional stress. Similarly, submit the structures in suspension to a flow in which extension is large, as uniform as possible, and persistent. A representative flow of this type is produced by the apparatus (Drawing 6) described by Berry and Mackley in "Six-roll mill—unfolding an unstable persistently extensional flow" for the study of the effect of extensional flow on dilute polymer solutions, and in "Catastrophe theory and its Applications" by Poston and Stewart. The fluid moves between six symmetrically placed rollers 401 of radius $r_r$, with axes 402 parallel to the z-axis 403, at a common distance R from that axis. Defining q as the square root of ¾, by choice of coordinates these axes 402 may be taken as containing points (R,0,0), (R/2,Rq,0), (-R/2,Rq,0), (-R,0,0), (-R/2,-Rq,0) and (-R/2,-Rq,0). The rollers rotate in alternating senses at angular velocities of $a_+$, $a_-$, $a_+$, $a_-$, $a_+$ and $a_-$ respectively, where $a_-$ is approximately equal to the negative of $a_+$. Choice of exact equality produces a structurally unstable flow (seen from above in Drawing 7, left), where three directions flow into the z-axis and three flow out: small errors can modify this flow in complex ways. A more robust effect is achieved by using a small planned difference between $a_+$ and $a_-$, which results in a central eddy (Drawing 7, right) of diameter proportional to $|a_+-a_-|$ and direction of turn fixed by the sign of $(a_+-a_-)$. This flow pattern is robust, and thus more easily controlled. The polynomial form which dominates the Taylor expansion of the flow potential around (0,0) is necessarily of the form $$\phi = x^3 - 3xy^2 + A(x^2+y^2) + Bx + Cy, \tag{31}$$

where A, B and C are system parameters adjustable by differences in the roller speeds, vanishing when all six are equal up to sign. Symmetry arguments show that with the above alternating speeds, B and C must vanish, and when $a_+=a_-$, so must A. A is thus a function $A=k_1(a_+-a_-)+k_2(a_+-a_-)^2+\ldots$, which we may approximate by $k_1(a_+-a_-)$ for small speed differences, fitting the constant k by empirical measurements of rotation rate at the center as a function of $(a_+ - a_-)$. The corresponding flow is $$V(x,y) = (6xy - 2Ay - C, \; 3x^2 - 3y^2 + 2Ax + B) \tag{32}$$

$$\underline{V}_p = \begin{bmatrix} 6y & 6x - 2A \\ 6x + 2A & -6y \end{bmatrix} \tag{33}$$

$$\underline{V}^R = \begin{bmatrix} 0 & -2A \\ 2A & 0 \end{bmatrix} \tag{34}$$

$$\underline{V}^S = \begin{bmatrix} 6y & 6x \\ 6x & 6y \end{bmatrix} \tag{35}$$

This is uniformly rotational, with constant $\underline{V}^R$ that vanishes when $a_+ = a_-$. Its shear level S is 6r, and its persistent strain level P is $6\sqrt{|r^2 - 4A^2/9|}$, equal to S when $a_+ = a_-$. By combining cell damage rate results from this and the Poiseuille configuration above, where S and P are strongly unequal, we may use standard statistical fitting to estimate the joint damaging effects of shear and extensional stress for various times of exposure. We can then define limit levels and times of exposure to extensional and shear stress, to remain above target levels of predicted cell failure from these causes.

Catheter Design

In the present invention we derive also the values in the flow field of shear and extension (Drawing 6, left and right respectively), and add to the criteria of the previous invention the conditions that the predicted loss of viability from shear and extensional stress should be within a range defined by medical experience.

Further, by testing and validating a wide range of such simulations, the present invention allows the establishment of general limits on imposed flow rates and pressures in injection protocols for each catheter design manufactured, which ensure that for all patients a protocol within said general limits will not cause a flow in which loss of viability from shear and extensional stress is within an acceptable range.

Catheter Deployment

U.S. Pat. Nos. 6,061,587 and 6,026,316; and U.S. patent application Ser. No. 09/754,039, filed Dec. 20, 2000 describe various aspects of technology useful in therapeutic material delivery and a process of planning a procedure to deliver concentrations of injected material, and levels of pressure and edema, to within desired ranges at different locations in the tissue of a particular patient for whom image and sometimes scout injection data are available. This process, with varying levels of automation, involves selecting a catheter model among the range of models and adjustments possible for the catheters supplied by the manufacturer, and an injection protocol for the particular patient, predicting the resulting flow and material transport, deriving the values for concentration, pressure and edema, and adjusting the design and protocol until these derived quantities are within the acceptable ranges. The protocol can then be followed, using image guidance to ensure that the results remain within target ranges.

In the present invention, we derive also the values in the flow field of shear and extension, and add to the criteria of the previous invention the conditions loss of viability from shear and extensional stress should be within a range defined by medical experience.

Further, in the absence of image guidance (as described in U.S. Pat. Nos. 6,061,587 and 6,026,316), the clinician selecting an injection protocol is equipped, by staying within the general limits established by the manufacturer as above, to ensure that loss of viability from shear and extensional stress should be within a range that enhances the probability of survival for the injected structures.

Motion and Reattachment in Tissue

As noted in the discussion of bolus flow above, the cells may be surrounded either by the main carrier fluid, or by a second fluid that encourages mutual attachment. Either fluid, moreover, may contain one or more substances that improve the chances that a cell will survive and attach itself as desired, such as vitamins, minerals, enzymes, hormones, enhancers, growth factors or the like: collectively, we will call these adjuvants. In general, each fluid and adjuvant will have different passive transport properties from the cells, and even from each other. (We ignore here the active self-transport of the cells, which is a longer-term process) Molecular weights, interactions with the substrate, etc., will vary considerably.

The patent application A METHOD AND APPARATUS FOR TARGETING MATERIAL DELIVERY TO TISSUE, U.S. patent application Ser. No. 566,478, filed May 8, 2000, describes a process of computing the flow of materials injected into a tissue such as the brain, by partial differential equation methods whose coefficients may be derived from scan data. Increasingly, biological experiment will give optimum ranges for a particular adjuvant, at the point of passive deposition. (This may not be the point of final attachment—indeed, the function of an adjuvant may to mobilize the cell for self-transport to an appropriate location.) We compute the predicted diffusion of each adjuvant from its concentration in the injected material, the ratio of the quantity of cell-carrying second liquid phase (if any) to that of the other, and from the mechanics of the injection and transport processes. We then adjust these concentrations and the said ratio until the predicted outcome in the target region gives adjuvant levels in the optimum range.

Flow of the Method

Figure 9:
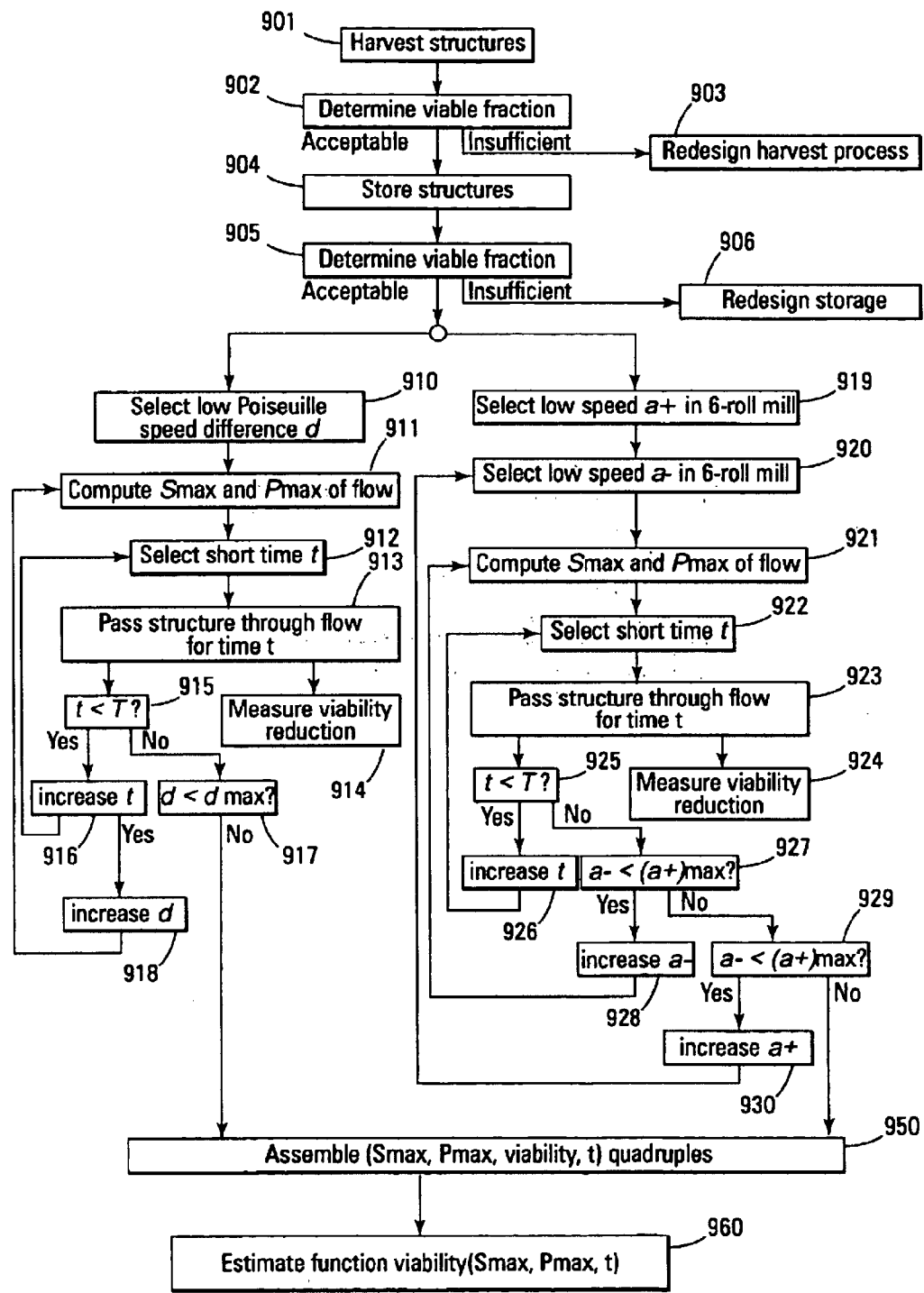
FIG. 9 shows a flow chart for the process of determining reduction of structural viability as a function of extensional and shear stress, and time of exposure.

The first stage in the method is to quantify survival at all stages previous to their arrival in tissue, as shown in FIG. 9. We harvest 901 the cells or other structures from the medium in which they are created or grown, and assess 902 the fraction which are viable, by a test appropriate to the particular type of structure involved. If the viable percentage is too low, we redesign 903 the harvest process, including perhaps a revision of the growth or manufacture medium or process to enable a more successful harvest. The structures must be stored 904 for transport to the injection site or for longer periods: we assess 905 their viability after an appropriate period of such storage, and redesign 906 our storage methods if the viable fraction is too low. Once we have a sufficient viable fraction for structures taken from storage, we estimate the surviving viable fraction viability $(S_{max}, P_{max}, t)$ as a function of the maximum shear and extensionality stresses to which cells are exposed for time t.

This requires that we perform a sequence of experiments in which we set 910 a speed difference d for the Poiseuille cylinders, and compute 911 the maxima $S_{max}$ and $P_{max}$ over the corresponding flows. We then select a short time t, then 912 insert the structures into the flow and extract them t later, repeating 915 and 916 up to a maximum time T. As an alternative organization, we may insert one population of structures and extract samples at times t, 2t, etc., from the flow. For each sample we measure the fraction of viable structures. When this sequence is complete, we increase 918 the driving speed difference d of the cylinders and repeat until 917 a maximum value D suggested by experience is reached.

Similarly, we select 920 roller speeds $a_+$ and $a_-$ for the roller sets in the 6-roll mill, compute 921 the maxima $S_{max}$ and $P_{max}$ over the corresponding flow, select 922 a starting time t which we will increase in steps, and 923 pass structures through the flow, gathering samples exposed to it for each time and 924 assessing the viable fraction. If a is less 929 than a preset maximum $a_{max}$ we increase it 930, and repeat the measurements: when $a_-$ reaches $a_{max}$ we reset it 920 after increasing $a_+$, until 929 $a_+$ reaches $a_{max}$. We then assemble 950 the quadruples ($S_{max}$, $P_{max}$, t, viable fraction) recorded from all these experiments, and estimate 960 the function viability ($S_{max}$, $P_{max}$, t) sampled by these data points, using least squares fitting or other methods well known to those skilled in the art. This function plays a key role in the insertion procedure, described next.

Figure 10:
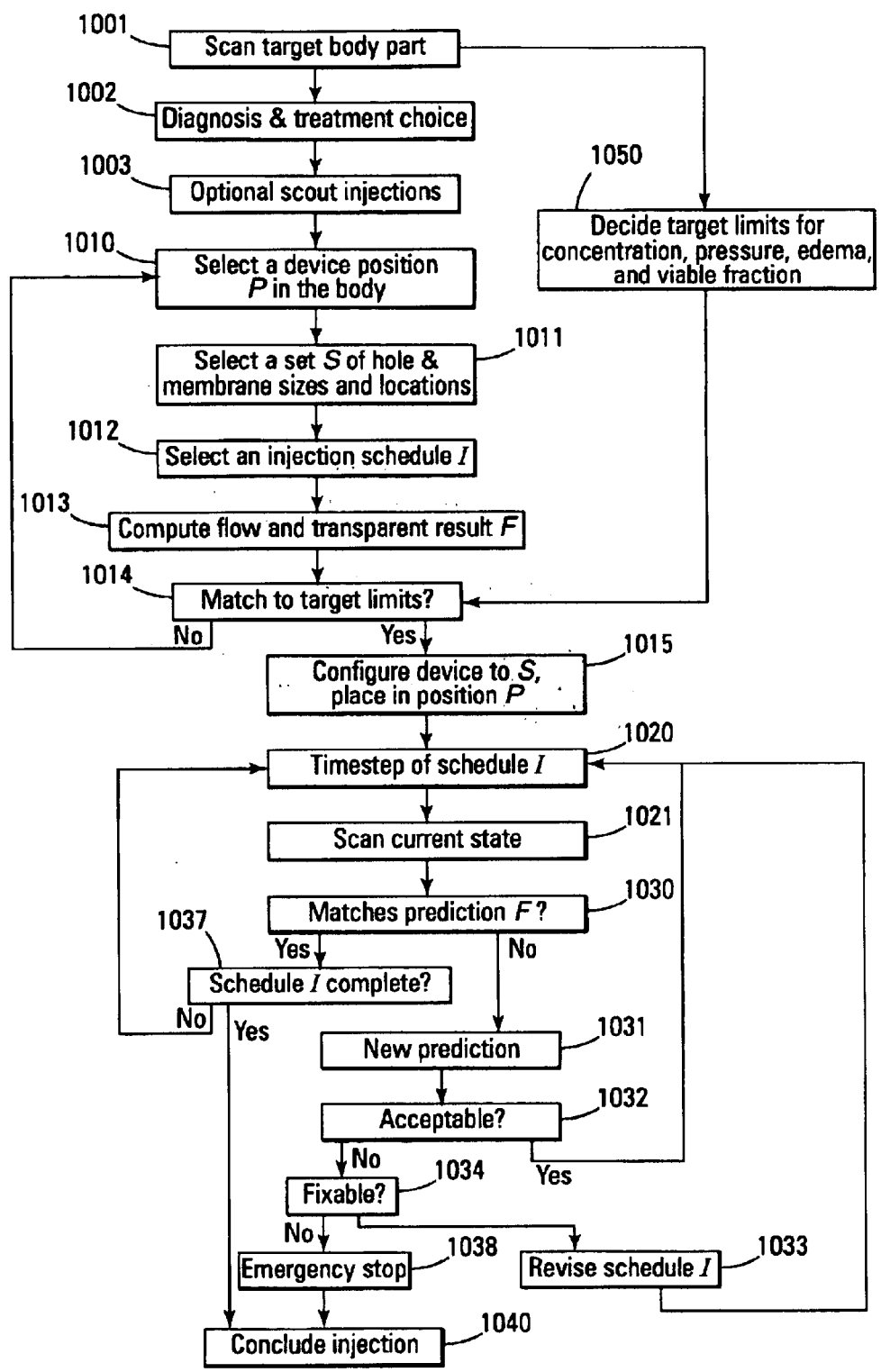
FIG. 10 shows a flow chart for the clinical process.

As shown in FIG. 10, the procedure begins with a scan 1001 of the target body part. The physician selects 1002 a diagnosis and treatment, using the scan data as convenient, but for the present purposes the scan represents information for planning an insertion procedure. If the physician selects the insertion of cells or other small structures, target limits must be set 1050 for the concentrations of structures and any adjuvant materials, pressure, edema, and viable fraction of cells. The process may optionally proceed 1003 by the administration of some scout injections, whose transport is imaged to provide additional data for transport modeling as in A METHOD AND APPARATUS FOR TARGETING MATERIAL DELIVERY TO TISSUE, U.S. patent application Ser. No. 566,478, filed May 8, 2000. The physician then selects 1010 a device position P from which the injection is to enter the tissue, defines 1011 a set S of parameters defining the delivery device], and determines 1012 an injection schedule I. The system then computes 1013 a predicted flow F, together with values for concentrations, pressure, edema, and shear and extensional stresses S and P with the stress exposure time t, from which viability (S, P, t) gives a predicted viable fraction of structures. If these meet 1014 the limits set in step 1050, the procedure continues: if not, it returns to step 1010 and a revised plan. (As in A METHOD AND APPARATUS FOR TARGETING MATERIAL DELIVERY TO TISSUE, U.S. patent application Ser. No. 566,478, filed May 8, 2000, this cycle may be automated to varying extents.)

If the target limits are predicted to be met, the next step 1015 is to configure the insertion device to S and manipulate it to achieve position P. In each timestep 1020 of schedule I, the current state is scanned 1021, and tested 1030 for its match to the prediction F. If to within tolerance it matches 1037 the schedule has been completed and the process concludes 1040, else 1031 a new prediction is made with updated information on concentrations and new estimates of transport coefficients, and tested 1032 as in 1013 and 1014 for acceptability. If it is not, the process applies 1034 a test for whether the problem justifies an emergency stop 1038 leading to termination 1040, or to a schedule revision 1033 and a return to the timestep repetition point 1020.

What is claimed:

1. A method for evaluating the performance of a device for the delivery of cells in a flow delivery cell implantation therapy comprising:

determining a first rate of cell survival in an environment, evaluating a second rate of survival in said environment during a procedure using a device that manipulates cells, and comparing the first and second rates of survival in said environment to determine the effect of the device used during said procedure on cell survival rates to establish a base line effect of manipulating cells using that device on cell survivability.

2. The method of claim 1 wherein the procedure includes a peristalsis process for movement of cells during the method.

3. The method of claim 1 wherein the procedure includes a bolus flow of cells for movement of cells during the method.

4. A method according to claim 1 wherein the procedure comprises the delivery of cells for cell implantation comprising transporting cells for delivery into a live patient issue by a process that includes determining survivability limits by at least one comparison with cell damage resulting from transporting means wherein flow of cells is generated by enclosing a fluid carrying cells between two concentric parallel cylinders, which may be caused to rotate at different speeds.

5. The process of claim 4 wherein where said flow is generated instead by enclosing the fluid in a tank containing six parallel rollers symmetrically placed in or near to a regular hexagonal arrangement, with approximately equal radii, of which three rotate clockwise and the rest placed between them, rotate anticlockwise, at approximately equal rates.

6. The process of claim 4 wherein the said survivability limits are determined by subjecting the cells to flows of both types, so that the damage limits for shear and extensional flow may be separately determined.

7. The process of claim 4 wherein the said survivability limits are determined by subjecting the cells to flows of both types, so that the damage limits for shear and extensional flow may be separately determined.

* * * * *